United States Patent [19]

Bonda et al.

[11] Patent Number: 5,783,173
[45] Date of Patent: Jul. 21, 1998

[54] STABLE SUNSCREEN COMPOSITION CONTAINING DIBENZOYLMETHANE DERIVATIVE, E. G., PARSOL 1789, AND C12, C16, C18, BRANCHED CHAIN HYDROXYBENZOATE AND/OR C12, C16, BRANCHED CHAIN BENZOATE STABILIZERS/SOLUBILIZERS

[75] Inventors: Craig A. Bonda, Wheaton; Steven P. Hopper, Glen Ellyn, both of Ill.

[73] Assignee: The C. P. Hall Company, Chicago, Ill.

[21] Appl. No.: 752,585

[22] Filed: Nov. 21, 1996

[51] Int. Cl.⁶ .............. A61K 7/42; A61K 31/24; A61K 31/12

[52] U.S. Cl. .............. 424/59; 424/60; 424/400; 424/401; 514/537; 514/679; 560/64; 560/103; 568/331

[58] Field of Search ................ 424/59, 60, 400, 424/401; 514/537, 679; 560/64, 103; 568/331

[56] References Cited

U.S. PATENT DOCUMENTS

| | | | |
|---|---|---|---|
| 4,323,694 | 4/1982 | Scala, Jr. | 560/103 |
| 4,387,089 | 6/1983 | De Polo | 424/59 |
| 4,489,057 | 12/1984 | Welters et al. | 424/47 |
| 4,562,067 | 12/1985 | Hopp et al. | 424/59 |
| 5,116,604 | 5/1992 | Fogel et al. | 424/59 |
| 5,670,140 | 9/1997 | Deflandre et al. | 424/59 |

OTHER PUBLICATIONS

Finetex® Technical Data Sheet, FINSOLV® TN, Finetex Inc. (New Jersey corporation), 148 Falmouth Avenue, Elmwood Park, NJ 07407.

U.S. Trademark Registration No. 1,730,483 registered Nov. 10, 1992 for the mark "FINSOLV", Finetex Inc., (New Jersey corporation), 148 Falmouth Avenue, Elmwood Park, NJ 07407.

*Primary Examiner*—Shelley A. Dodson
*Attorney, Agent, or Firm*—Marshall, O'Toole, Gerstein, Murray & Borun

[57] ABSTRACT

A sunscreen composition containing a UV-B dibenzoylmethane derivative, such as 4-(1,1-dimethylethyl)-4'-methoxydibenzoylmethane (PARSOL 1789), and a stabilizer/solubilizer for the dibenzoylmethane derivative selected from formula (I) and formula (II), and mixtures thereof:

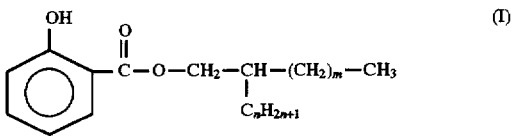

wherein m=5, 7, 9 or mixtures and n=4, 6, 8 or mixtures;

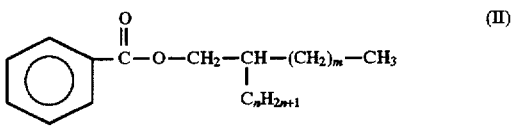

wherein m=5, 7 or mixtures and n=4, 6 or mixtures.

These long branched chain alkyl hydroxybenzoates and long branched chain benzoates having a $C_4^+$ branch at the 2 position are quite effective in stabilizing the dibenzoylmethane derivative UV-B filter compounds making them more effective; effective for longer periods of time.

23 Claims, No Drawings

STABLE SUNSCREEN COMPOSITION CONTAINING DIBENZOYLMETHANE DERIVATIVE, E. G., PARSOL 1789, AND C12, C16, C18, BRANCHED CHAIN HYDROXYBENZOATE AND/OR C12, C16, BRANCHED CHAIN BENZOATE STABILIZERS/SOLUBILIZERS

FIELD OF THE INVENTION

The present invention is directed to a stable sunscreen composition for topical application to human skin to protect the skin against UV radiation damage. More particularly, the present invention is directed to the use of long chain ($C_{12}$, $C_{16}$ and/or $C_{18}$) branched alkyl hydroxybenzoates and/or long chain ($C_{12}$, $C_{16}$) branched chain alkyl benzoates that are surprisingly effective in stabilizing dibenzoylmethane derivatives, particularly 4-(1,1-dimethylethyl)-4'-methoxydibenzoylmethane (PARSOL 1789) such that the PARSOL 1789 is a more effective sunscreen, having a surprisingly increased sunscreen protection factor (SPF) and such that the PARSOL 1789 is more effective over a longer period of time so that the sunscreen composition need not be applied to the skin as frequently.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles. Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or PARSOL MCX, having an ethyl radical extending from the 2 position of the hexyl long chain backbone; and octyl salicylate.

The UV-A filters most commonly used in commercial sunscreen compositions are the dibenzoylmethane derivatives, particularly 4-(1,1-dimethylethyl)-4'-methoxydibenzoylmethane (PARSOL 1789), and 4-isopropyl dibenzoylmethane (EUSOLEX 8020). Other dibenzoylmethane derivatives described as UV-A filters are disclosed in U.S. Pat. Nos. 4,489,057; 4,387,089 and 4,562,067, hereby incorporated by reference. It is also well known that the above described and most commonly used UV-A filters, particularly the dibenzoylmethane derivative, such as PARSOL 1789, suffer in photochemical stability when combined with the above-described most commercially used UV-B filters. Accordingly, when a UV-B filter, such as 2-ethylhexyl paramethoxycinnamate (PARSOL MCX), and/or octyl salicylate, is combined with the dibenzoylmethane derivative UV-A compounds, such as PARSOL 1789, the PARSOL 1789 becomes less photochemically stable necessitating repeated, frequent coatings over the skin for sufficient UV radiation protection.

In accordance with the principles of the present invention, it has been found, quite surprisingly, that by including a $C_{12}$, $C_{16}$, $C_{18}$ branched chain hydroxybenzoate of formula (I), preferably $C_{12}$ branched chain hydroxybenzoate, and/or a $C_{12}$, $C_{16}$ branched chain benzoate of formula (II) into a cosmetic sunscreen formulation containing a UV-A dibenzyolmethane derivative, particularly PARSOL 1789, or EUSOLEX 8020, the dibenzyolmethane derivative is photochemically stabilized so that the dibenzyolmethane derivative-containing sunscreen composition is more effective for filtering out UV-A radiation; the composition filters UV-A radiation for longer periods of time; and, therefore, the sunscreen formulation need not be applied to the skin as frequently while maintaining effective skin protection against UV-A radiation:

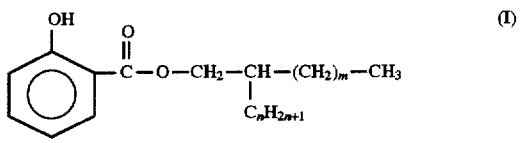

wherein m=5, 7, 9 or mixtures
and n=4, 6, 8 or mixtures;

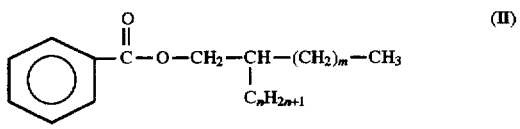

wherein m=5, 7 or mixtures
and n=4, 6 or mixtures.

By the addition of the UV-B filter compounds, the cosmetic sunscreen formulation can maintain surprisingly effective skin protection against UV radiation both in the UV-A and UV-B range, with or without common sunscreen additives, such as benzophenone 3, octocrylene, and/or titanium dioxide. The ratio of UV-A to UV-B filter compounds is in the range of about 0.1:1 to about 3:1, preferably about 0.1:1 to about 0.3:1, most preferably about 0.24:1.

SUMMARY OF THE INVENTION

In brief, the present invention is directed to sunscreen compositions containing a dibenzoylmethane derivative UV-A filter compound, such as 4-(1,1-dimethylethyl)-4'-methoxydibenzoylmethane (PARSOL 1789), and a stabilizer/solubilizer for the dibenzoylmethane derivative selected from formula (I) and formula (II), and mixtures thereof:

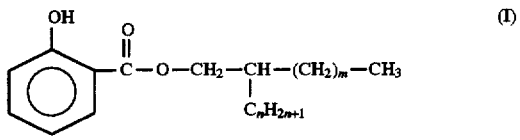

wherein m=5, 7, 9 or mixtures
and n=4, 6, 8 or mixtures;

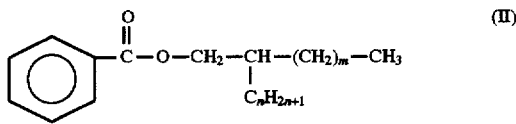

wherein m=5, 7 or mixtures
and n=4, 6 or mixtures.

Surprisingly, it has been found that these long branched chain alkyl hydroxybenzoates and long branched chain (2 position) benzoates having at least $C_4$ branches at the 2 position are quite effective in stabilizing the dibenzoylmethane derivative UV-B filter compounds making them more effective; effective for longer periods of time; and, therefore, the sunscreen composition need not be reapplied as frequently to maintain effective UV radiation skin protection.

Accordingly, one aspect of the present invention is to provide a stable sunscreen composition that includes a stabilizer/solubilizer compound selected from formula (I), formula (II), or mixtures capable of stabilizing a dimethylbenzoyl derivative UV-A filter, particularly PARSOL 1789:

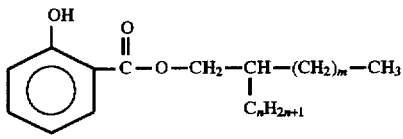
(I)

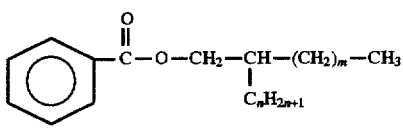
(II)

Another aspect of the present invention is to provide stabilizer compounds for dimethylbenzoyl derivatives, particularly PARSOL 1789, and methods of manufacturing the stabilizer compounds, capable of stabilizing the dimethylbenzoyl derivatives, and capable of increasing the sunscreen protection factor (SPF) achievable for sunscreen compositions containing the dimethylbenzoyl derivatives to a SPF of at least 20, particularly 20–25 SPF.

Another aspect of the present invention is to provide a stable sunscreen composition that has a SPF of at least 20, without a sunscreen composition additive selected from the group consisting of benzophenone 3, octocrylene or other substituted dialkylbenzalmalonates or substituted dialkylmalonates.

Still another aspect of the present invention is to provide an improved, stable sunscreen composition containing 2-butyloctyl benzoate and/or 2-hexyldecyl benzoate, particularly a 40%, 60% by weight mixture, respectively, having a refractive index of at least about 1.40, particularly about 1.45 to about 1.48, that increases the effectiveness of dimethylbenzoyl derivative sunscreen compounds, particularly 4-(1,1-dimethylethyl)-4'-methoxydibenzoylmethane (PARSOL 1789), in SPF and in duration.

Another aspect of the present invention is to provide an improved, stable sunscreen composition containing 2-butyloctyl hydroxybenzoate, having a refractive index of about 1.49, that increases the effectiveness of dimethylbenzoyl derivative sunscreen compounds, particularly 4-(1,1-dimethylethyl)-4'-methoxydibenzoylmethane (PARSOL 1789), in SPF and in duration.

The above and other aspects and advantages of the present invention will become more apparent from the following detailed description of the preferred embodiments.

DETAILED DESCRIPTION OF THE PREFERRED EMBODIMENTS

The sunscreen compositions of the present invention include about 1% to about 3% of a dibenzoylmethane derivative UV-A filter compound, such as 4-(1,1-dimethylethyl)-4'-methoxydibenzoylmethane (PARSOL 1789) and about 1% to about 10% by weight of a stabilizer/solubilizer for the dibenzoylmethane derivative, selected from the group consisting of formula (I), formula (II), and mixtures thereof:

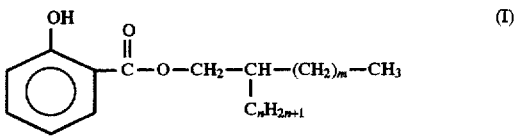

wherein m=5, 7, 9 or mixtures
and n=4, 6, 8 or mixtures;

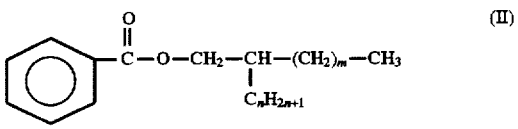

wherein m=5, 7 or mixtures
and n=4, 6 or mixtures.

The compounds of formula (I) and formula (II) are formed by typical esterification and transesterification reactions as follows:

FORMULA (I):
1. HYDROXYBENZOATE ESTERIFICATION REACTION

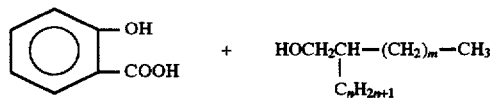

2-Hydroxybenzoic Acid where m=5, 7, 9 or mixtures
and n=4, 6, 8 or mixtures

| Methane Sulfonic Acid
↓ (M.S.A.) catalyst

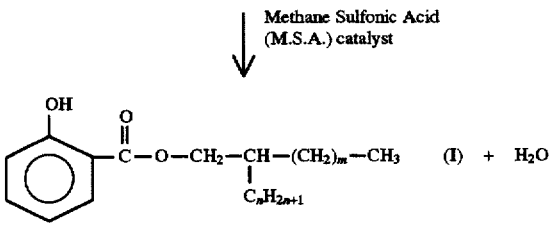
(I) + H$_2$O wherein m=5, 7, 9 or mixtures
and n=4, 6, 8 or mixtures
preferred where m=5 and n=4:

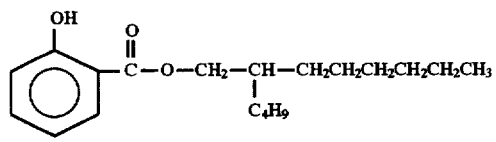

2-Butyloctyl Hydroxybenzoate
(Refractive Index = 1.49)

| Loading Formula For 2-Butyloctyl Hydroxybenzoate (preferred Formula (I)) Synthesis | |
|---|---|
| REACTANTS | WEIGHT % |
| Hydroxybenzoic Acid | 40.3 |
| 2-Butyloctanol (ISOFOL 12) | 59.7 |

-continued

| Loading Formula For 2-Butyloctyl Hydroxybenzoate (preferred Formula (I)) Synthesis | |
|---|---|
| REACTANTS | WEIGHT % |
| M.S.A.* (99.9%) | 0.2 |
| Sodium Hypophosphite | 0.015** |

*Methane sulfonic acid catalyst
**Based on the weight of hydroxybenzoic acid

FORMULA (II):

1. BENZOATE ESTERIFICATION REACTION

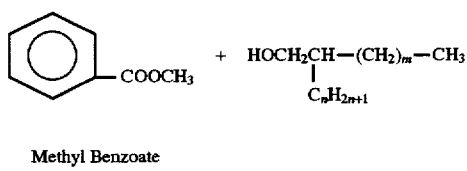

Methyl Benzoate wherein m=5, 7 or mixtures and n=4, 6 or mixtures

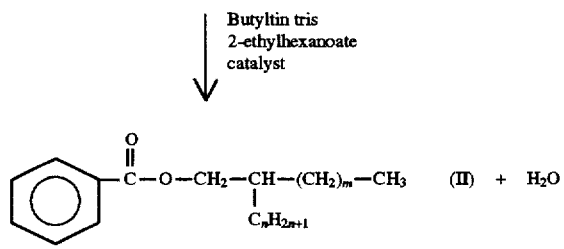

wherein m=5, 7 or mixtures and n=4, 6 or mixtures preferred mixtures are 40% by weight: m=5, n=4; 60% by weight: m=7, n=6:

40% by weight 2-butyloctyl benzoate:

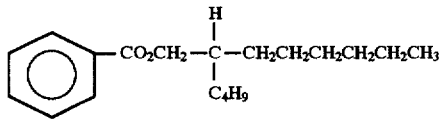

2-Butyloctyl Benzoate

60% by weight 2-hexyldecyl benzoate:

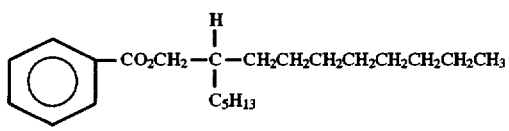

2-Hexyldecyl Benzoate

The 40%/60% mixture has a refractive Index of 1.48.

| Loading Formula For 40% 2-Butyloctyl Benzoate/60% 2-Hexyldecyl Benzoate | |
|---|---|
| REACTANTS | WEIGHT % |
| Methylbenzoate | 40.8 |
| 2-Butyloctyl alcohol (ISOFOL 12) | 22.4 lbs. |
| 2-Hexyldecyl alcohol (ISOFOL 16) | 36.8 lbs. |
| Catalyst Fascat 9102* | 0.03%** |
| Sodium Hypophosphite | 0.015%** |
| SORBAMOL | 1.5%** |
| Dicalite | 0.75%** |

*Butyltin tris 2-ethylhexanoate catalyst
**Based on the weight of methyl benzoate + alcohols After loading the raw materials, agitation, nitrogen sparge and heat were turned on in a glass reaction kettle. Sodium hypophosphite was added on loading. At 290° F. the catalyst was added and heating was continued. Reaction started in the 380°–385° F. range as manifested by the evolution of MeOH. The overhead temperature was maintained at 140°–145° F. during the generation of MeOH. This was accomplished by controlling the reflux at 1:2 ratio. The reflux ratio indicates one fraction of the overhead product is taken out as a distillate product and two fractions goes back to the reaction kettle as reflux. This is the ratio found to be ideal to control the overhead temperature.

Heat was continued to a maximum reaction temperature of 420° F. When the overhead temperature dropped to 130°–135° F., the column was switched off and the reaction was continued on by-pass. Kettle samples were checked for acid value, color and percent alcohol. Vacuum was applied when the methyl alcohol content dropped to 2% by weight. Partial vacuum was applied initially to prevent foam over, then gradually increased to full as conditions permitted. Stripped for methylbenzoate until 0.10% by weight. At this time methylbenzoate odor was very faintly detectable. Cooled down the glass-lined reaction kettle to 180° F.

It is preferred to treat the product with a color body-absorbing compound, such as an activated charcoal or acid-activated calcium montmorillonite clay, to improve the color. The product required three separate activated charcoal treatments using 1% charcoal (based on batch initial weight) for each treatment to bring color down to 30–40 APHA. On the other hand, only one treatment with an acid-activated calcium montmorillonite clay (SORBAMOL) was required, in an amount of 1.26 based on the initial weight of the batch, to improve color to 20 APHA. All post treatment decolorizing steps were done at 180° F. and mixed for one hour, and then the batch was filtered with Dicalite.

The finished product was then analyzed and the results are as follows:

| Appearance | Clear |
|---|---|
| Acid Value | 0.01 |
| Color, APHA | 30–40 |
| Water, % | 0.03 |
| Saponification Value | 175.7 |
| Specific Gravity | 0.92 |
| Refractive Index | 1.48 |

The compounds of formula (I) and/or formula (II) are combined with the well-known moisturizers, emollients, solvents, lubricants, emulsifiers and other common cosmetic formulation ingredients for solubility of formulas (I) and (II), emulsification, thickening agents, and to provide other skin enhancement, e.g., moisturizing properties, as well known in the art. The compositions can be produced as oily lotions, gels, solid sticks, emulsions, aerosols, and all other forms of cosmetic compositions. The compositions of the following examples provide exceptional skin feel and moisturizing properties in comparison to typical prior art sunscreen compositions.

EXAMPLE 1

Oil-in-water emulsion

| PHASE | CHEMICAL NAME | TRADE NAME | % W/W | FUNCTION |
|---|---|---|---|---|
| A | Octyl methoxycinnamate | Escalol 557[7] | 7.50 | UVB sunscreen |
| A | Octyl salicylate | Dermoblock OS[4] | 5.00 | UVB sunscreen |
| A | Butyloctyl hydroxybenzoate | HallBrite ™ BHB[1*] | 5.00 | Emollient, stabilizer/solvent |
| A | $C_{12}/C_{16}$ alkyl benzoate | HallStar ™ AB[1*] | 5.00 | Emollient, stabilizer/solvent |
| A | Avobenzone | PARSOL 1789[3] | 3.00 | UVA sunscreen |
| B | PVP/Eicosene copolymer | Ganex V-220[7] | 1.00 | Moisture barrier |
| B | Dimethicone copolyol | Silwet L-7087[6*] | 0.20 | Lubricant |
| B | Silica | Aerosil R972[11] | 0.50 | Thixotrope |
| B | Tocopheryl acetate | Vitamin E acetate[8] | 0.10 | Vitamin |
| C | Deionized water | Water | Q.S. | Solvent, carrier |
| C | Disodium EDTA | Disodium EDTA | 0.05 | Chelator |
| C | Butylene glycol | Butylene glycol* | 2.00 | Humectant, solvent |
| C | Phenoxyethanol() methylparaben() ethylparaben() propylparaben() butylparaben | Phenonip[2] | 0.60 | Preservative |
| C | Glycerin | Glycerin* | 4.00 | Humectant |
| D | Acrylates/$C_{10-30}$ alkyl acrylates crosspolymer | Pemulen TR-1[9] | 0.25 | Emulsifier |
| D | Carbomer | Carbopol Ultrez[9] | 0.20 | Thickener, stabilizer |
| D | Hydroxypropyl methocellulose | Primaflo MP3295A[10] | 0.20 | Film former |
| D | Polysorbate 80 | Tween 80[5] | 0.040 | Particle size reducer |
| D | Panthenol (50%) | DL-Panthenol[8] | 0.50 | Moisturizer, soothant |
| E | Triethanolamine (99%) | Triethanol-amine* | Q.S. to pH 5.5 | Neutralizer |

[1]The C.P. Hall Company, Inc.;
[2]Nipa;
[3]Givaudan Rohr;
[4]Alzo;
[5]ICI;
[6]OSi;
[7]ISP;
[8]Roche;
[9]B.F. Goodrich;
[10]Aqualon;
[11]DeGussa
*Available from The C.P. Hall Company, Inc.
*UVA/UVB Ratio of 0.80 determined by Optometrics SPF 290.

Preferred Mixing Sequence For All Examples:

1. Stir "A" additives until avobenzone is completely dissolved. Add "B" additives to "A". Heat to 65° C. with stirring to disperse silica and melt and dissolve solids.

2. Add "C" additives to water in order shown, dissolving the Phenonip in the butylene glycol before the addition.

3. To water phase ("C"), add "D" ingredients in order shown, dispersing and wetting the solids according to manufacturer's instructions. Stir 30 minutes and heat to 65° C.

4. With vortex stirring, add Oil Phase ("A", "B") to Water Phase ("C", "D").

5. Remove heat from emulsion and allow to cool while stirring. When temperature is below 50, slowly add "E" to pH 5.5 or until desired viscosity is reached. Add fragrance. Stir to a smooth cream.

Significantly, the extremely high SPF rating is achieved without oxybenzone (benzophenone 3), octocrylene, or titanium dioxide. Instead, it uses two new additives for advanced sunscreen formulations, HallBrite BHB and HallStar AB. HallBrite BHB adds unique emolliency and solvency for avobenzone (PARSOL 1789). HallStar AB is an outstanding emollient and solvent for avobenzone that will not freeze even as temperatures fall below −20° C.

EXAMPLE 2

Oil-in-water emulsion

| PHASE | CHEMICAL NAME | TRADE NAME | % W/W | FUNCTION |
|---|---|---|---|---|
| A | Octyl methoxycinnamate | Escalol 557[7] | 7.50 | UVB sunscreen |
| A | Octyl salicylate | Dermoblock OS[4] | 5.00 | UVB sunscreen |
| A | Butyloctyl hydroxybenzoate | HallBrite ™ BHB[1*] | 3.00 | Emollient, solvent |
| A | $C_{12}/C_{16}$ alkyl benzoate | HallStar ™ AB[1*] | 3.00 | Emollient, solvent |
| A | Avobenzone | PARSOL 1789[3] | 1.00 | UVA sunscreen |
| B | PVP/Eicosene copolymer | Ganex V-220[7] | 1.00 | Moisture barrier |
| B | Dimethicone copolyol | Silwet L-7087[6*] | 0.20 | Lubricant |
| B | Silica | Aerosil R972[11] | 0.50 | Thixotrope |
| B | Tocopheryl acetate | Vitamin E acetate[8] | 0.10 | Vitamin |
| C | Deionized water | Water | Q.S. | Solvent, carrier |
| C | Disodium EDTA | Disodium EDTA | 0.05 | Chelator |
| C | Butylene glycol | Butylene glycol* | 2.00 | Humectant, solvent |
| C | Phenoxyethanol() methylparaben() ethylparaben() propylparaben() butylparaben | Phenonip[2] | 0.60 | Preservative |
| C | Glycerin | Glycerin* | 4.00 | Humectant |
| D | Acrylates/$C_{10-30}$ alkyl acrylates crosspolymer | Pemulen TR-1[9] | 0.25 | Emulsifier |
| D | Carbomer | Carbopol Ultrez[9] | 0.20 | Thickener, stabilizer |
| D | Hydroxypropyl methocellulose | Primaflo MP3295A[10] | 0.20 | Film former |
| D | Polysorbate 80 | Tween 80[5] | 0.40 | Particle size reducer |
| D | Panthenol (50%) | DL-Panthenol[8] | 0.50 | Moisturizer, soothant |
| E | Triethanolamine (99%) | Triethanol-amine* | Q.S. to pH 5.5 | Neutralizer |

EXAMPLE 3

Oil-in-water emulsion (mousse when in pressurized can with propellant)

| PHASE | CHEMICAL NAME | TRADE NAME | % W/W | FUNCTION |
|---|---|---|---|---|
| A | Octyl methoxycinnamate | Escalol 557[7] | 7.50 | UVB sunscreen |
| A | Octyl salicylate | Dermoblock OS[4] | 5.00 | UVB sunscreen |
| A | Butyloctyl hydroxybenzoate | HallBrite™ BHB[1*] | 8.00 | Emollient, solvent |
| A | Avobenzone | PARSOL 1789[3] | 3.00 | UVA sunscreen |
| B | PVP/Eicosene copolymer | Ganex V-220[7] | 0.25 | Moisture barrier |
| B | Dimethicone copolyol | Silwet L-7087[6*] | 0.40 | Lubricant |
| B | Silica | Aerosil R972[11] | 0.50 | Thixotrope |
| B | Tocopheryl acetate | Vitamin E acetate[8] | 0.10 | Vitamin |
| C | Deionized water | Water | Q.S. | Solvent, carrier |
| C | Disodium EDTA | Disodium EDTA | 0.05 | Chelator |
| C | Butylene glycol | Butylene glycol* | 2.00 | Humectant, solvent |
| C | Phenoxyethanol() methylparaben() ethylparaben() propylparaben() butylparaben | Phenonip[2] | 0.60 | Preservative |
| C | Glycerin | Glycerin* | 4.00 | Humectant |
| D | Acrylates/C$_{10-30}$ alkyl acrylates crosspolymer | Pemulen TR-1[9] | 0.25 | Emulsifier |
| D | Carbomer | Carbopol Ultrez[9] | 0.10 | Thickener, stabilizer |
| D | Hydroxypropyl methocellulose | Primaflow MP3295A[10] | 0.20 | Film former |
| D | Polysorbate 80 | Tween 80[5] | 0.40 | Particle size reducer |
| D | Panthenol (50%) | DL-Panthenol[8] | 0.50 | Moisturizer, soothant |
| D | Triethanolamine (99%) | Triethanol-amine* | Q.S. to pH 5.5 | Neutralizer |

What is claimed is:

1. A sunscreen composition for topical application to human skin for protection against ultraviolet radiation comprising, in a cosmetically acceptable carrier, 1% to 3% by weight of a dibenzoylmethane derivative and at least 1% by weight of a stabilizing compound selected from the group consisting of formula (I), formula (II), and mixtures thereof:

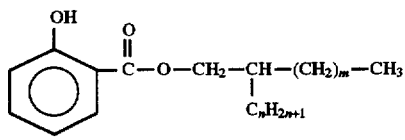

wherein m=5, 7, 9 or mixtures
and n=4, 6, 8 or mixtures;

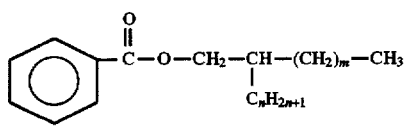

wherein m=5, 7 or mixtures
and n=4, 6 or mixtures.

2. A composition in accordance with claim 1, wherein the molar ratio of said stabilizing compound having formula (I) and/or formula (II) to said dibenzoylmethane derivative is about 0.1:1 to about 3:1.

3. A composition in accordance with claim 1, wherein the molar ratio of said stabilizing compound having formula (I) and/or formula (II) to said dibenzoylmethane derivative is about 0.1:1 to about 0.3:1.

4. A composition in accordance with claim 3, wherein said dibenzoylmethane derivative is selected from the group consisting of 4-(1,1-dimethylethyl)-4'-methoxydibenzoylmethane; 4-isopropyl dibenzoylmethane; and mixtures thereof.

5. A composition in accordance with claim 4, wherein the dibenzoylmethane derivative is 4-(1,1-dimethylethyl)-4'-methoxydibenzoylmethane.

6. A composition in accordance with claim 5, wherein the dibenzoylmethane derivative is included in the composition in an amount of about 2% to 3% by weight of the composition.

7. A composition in accordance with claim 6, wherein the stabilizing compound is included in the composition in an amount of about 1% to about 10% by weight of the composition, and the stabilizing compound is selected from the group consisting of 2-butyloctyl benzoate, 2-hexyldecyl benzoate, 2-butyloctyl hydroxybenrzoate, and mixtures thereof.

8. A composition in accordance with claim 7, wherein the stabilizing compound comprises a mixture of 2-butyloctyl benzoate and 2-hexyldecyl benzoate in a weight ratio of 2-butyloctyl benzoate to 2-hexyldecyl benzoate in the range of 1:3 to 1:1.

9. A composition in accordance with claim 8, wherein the weight ratio is about 2:3.

10. A composition in accordance with claim 8, further including 2-butyloctyl hydroxybenzoate, in an amount of about 1% to about 10% by weight of the composition.

11. A method of filtering out ultraviolet radiation from human skin comprising topically applying to said skin a composition, in a cosmetically acceptable carrier, comprising 1% to 3% by weight of a dibenzoylmethane derivative and at least 1% by weight of a stabilizing compound selected from the group consisting of formula (I), and formula (II), and mixtures thereof:

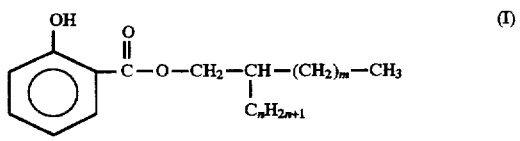

wherein m=5, 7, 9 or mixtures
and n=4, 6, 8 or mixtures;

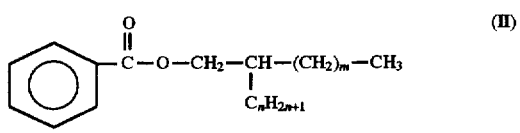

wherein m=5, 7 or mixtures
and n=4, 6 or mixtures.

12. A method in accordance with claim 11, wherein the molar ratio of said stabilizing compound having formula (I) and/or formula (II) to said dibenzoylmethane derivative is about 0.1:1 to about 3:1.

13. A method in accordance with claim 11, wherein the molar ratio of said stabilizing compound having formula (I) and/or formula (II) to said dibenzoylmethane derivative is about 0.1:1 to about 0.3:1.

14. A method in accordance with claim 13, wherein said dibenzoylmethane derivative is selected from the group consisting of 4-(1,1-dimethylethyl)-4'-methoxydibenzoylmethane; 4-isopropyl dibenzoylmethane; and mixtures thereof.

15. A method in accordance with claim 14, wherein the dibenzoylmethane derivative is 4-(1,1-dimethylethyl)-4'-methoxydibenzoylmethane.

16. A method in accordance with claim 15, wherein the dibenzoylmethane derivative is included in the composition in an amount of about 2% to 3% by weight of the composition.

17. A method in accordance with claim 16, wherein the stabilizing compound is selected from the group consisting of 2-butyloctyl benzoate, 2-hexyldecyl benzoate, 2-butyloctyl hydroxybenzoate, and mixtures thereof.

18. A method in accordance with claim 17, wherein the stabilizing compound comprises a mixture, in a total amount of about 1% to about 10% by weight of the composition, of 2-butyloctyl benzoate and 2-hexyldecyl benzoate in a weight ratio of 2-butyloctyl benzoate to 2-hexyldecyl benzoate in the range of 1:3 to 1:1.

19. A method in accordance with claim 18, wherein the weight ratio is about 2:3.

20. A method in accordance with claim 18, further including 2-butyloctyl hydroxybenzoate, in an amount of about 1% to about 10% by weight of the composition.

21. A composition having emollient and sunscreen activity comprising a mixture of a compound of formula (I) and a compound of formula (II) in a weight ratio of (I):(II) in the range of 1:3 to 3:1

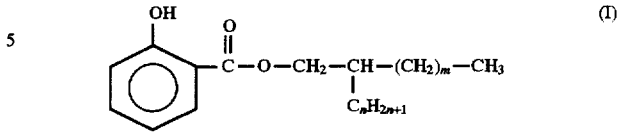

wherein m=5, 7, 9 or mixtures and n=4, 6, 8 or mixtures; and

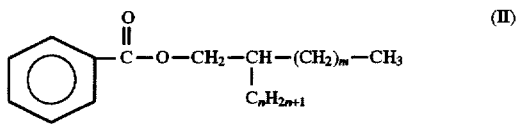

wherein m=5, 7 or mixtures and n=4, 6 or mixtures.

22. A composition in accordance with claim 21, wherein the compound of formula (II) includes a mixture of 2-butyloctyl benzoate and 2-hexyldecyl benzoate in a weight ratio of 1:3 to 1:1.

23. A composition in accordance with claim 22, wherein the weight ratio is about 2:3.

UNITED STATES PATENT AND TRADEMARK OFFICE
CERTIFICATE OF CORRECTION

PATENT NO. : 5,783,173
DATED : July 21, 1998
INVENTOR(S) : Bonda et al.

It is certified that error appears in the above-identified patent and that said Letters Patent is hereby corrected as shown below:

Column 6,
Line 48, after "in an amount of..." delete "1.26" and insert -- 1.2% --.

Signed and Sealed this

Eighteenth Day of December, 2001

*Attest:*

JAMES E. ROGAN
*Attesting Officer*     *Director of the United States Patent and Trademark Office*